United States Patent [19]

Schmidt et al.

[11] Patent Number: 4,816,412
[45] Date of Patent: Mar. 28, 1989

[54] METHOD FOR THE DETERMINATION OF THE CONTENT OF SOLID CARBON COMPOUNDS IN SOIL SAMPLES

[75] Inventors: Manfred Schmidt, Bruchköbel; Horst Fechter, Freising, both of Fed. Rep. of Germany

[73] Assignee: Leybold-Heraeus GmbH, Cologne, Fed. Rep. of Germany

[21] Appl. No.: 896,934

[22] Filed: Aug. 15, 1986

[30] Foreign Application Priority Data

May 22, 1986 [DE] Fed. Rep. of Germany ....... 3617246

[51] Int. Cl.$^4$ ............................................. G01N 31/10
[52] U.S. Cl. ........................................ 436/33; 436/31; 436/32; 436/145; 436/159; 436/160
[58] Field of Search .................................. 436/31–33, 436/145, 159, 160

[56] References Cited

U.S. PATENT DOCUMENTS

| 2,437,045 | 3/1948 | Roper | 436/32 |
| 2,470,401 | 5/1949 | Horvitz | 436/31 |
| 2,500,213 | 3/1950 | Stevens | 436/31 X |
| 2,962,360 | 11/1960 | Bennet et al. | 422/80 |
| 3,304,159 | 2/1967 | Hinsvark | 436/145 X |
| 3,305,318 | 2/1967 | Bennet | 436/145 |
| 3,428,432 | 2/1969 | Staunton et al. | 436/145 X |
| 3,508,877 | 4/1970 | Heacock et al. | 436/145 X |

Primary Examiner—Barry S. Richman
Assistant Examiner—Jill Johnston
Attorney, Agent, or Firm—Felfe & Lynch

[57] ABSTRACT

Method for the determination of the content of solid carbon compounds in soil samples, particularly in humus soils, by converting the solid carbon compounds with a reactant into carbon dioxide and conveying the carbon dioxide gas into an analyzer. To reach the reaction temperature, metal particles are added to a specified amount of the dry, milled soil sample and the dry matter is heated inductively in the presence of the reactant to the reaction temperature.

8 Claims, 1 Drawing Sheet

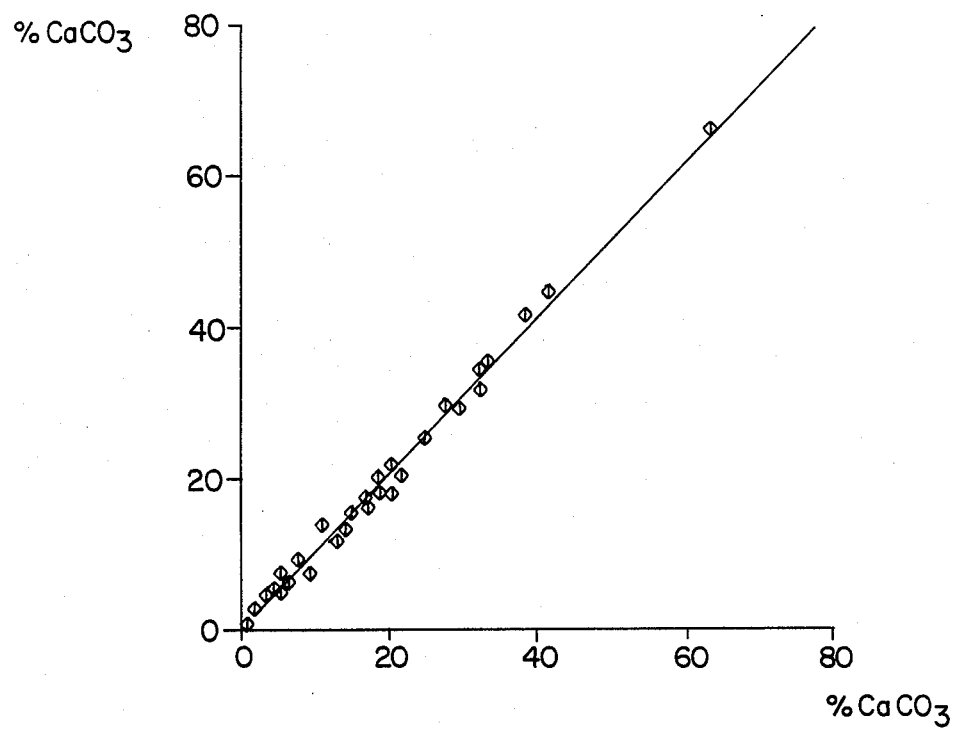

METHOD FOR THE DETERMINATION OF THE CONTENT OF SOLID CARBON COMPOUNDS IN SOIL SAMPLES

The invention relates to a method for the determination of the content of solid carbon compounds in soil samples, particularly in humus soils, by converting the solid carbon compounds with a reactant into carbon dioxide and conveying the carbon dioxide gas to an analyzer.

The analysis of soil samples plays an important role especially in agriculture, whether it be to establish the most appropriate type of planting or to draw up fertilizing plans. More particularly, in the last mentioned case, a knowledge of the humus content, which comprises organic substances, is important.

It is known that the determination of the humus content may be carried out in two separate analytical procedures. In the one analytical procedure, the total carbon content is determined by combustion at a very high temperature, at which the carbonates also decompose with release of their total carbon content in the form of carbon dioxide. The combustion is accomplished by supplying oxygen. In a second procedure, the so-called carbonate is determined using a second, identical soil sample. From the difference between the two measurements, conclusions can be drawn regarding the humus content. It is understood, that conclusions can be drawn from the amount of carbon dioxide measured with regard to the special carbon-containing components of the soil samples.

In the known combustion procedure, it is, however, difficult to produce a uniform reaction temperature and to initiate a uniform combustion process within the whole of the sample volume. This difficulty is associated with inaccurate test results, since the physical properties of such soil samples stand in the way of a rapid and uniform spread of the necessary reaction temperature.

Until now, the determination of the carbonate content of soil samples was even far more difficult. The analysis in question was carried out by wet-chemical means with the simultaneous, quantitative collection of the carbon dioxide released, the time taken for the analysis varying between 1 and 10 hours, depending on the nature of the soil samples. In general, the soil samples, in the form of an aqueous suspension, were decomposed by the addition of an aqueous or water-containing liquid acid, carbon dioxide being released and a salt formed from the corresponding metal and the radical of the acid used. Apart from the sophisticated analytical method used, it was not always possible to adhere with this method to the condition that the humus must not be attacked in the form in which it is present. A further disadvantage of the known method lay therein that the quantitative collection made it necessary to read the result. Moreover, the presence of water in the known method proved to be disadvantageous, because the moist carbon dioxide gas, before it was introduced into the analyzer, had to be freed carefully from water vapor in such a manner, that this process was not accompanied by absorption of carbon dioxide. Moreover, in view of the upper temperature limit that had to be taken into consideration, the reaction equipment was also correspondingly expensive.

It is therefore an object of the invention to improve and simplify a method of the type described at the outset, so that either the total carbon content or the carbonates content can be determined in a shorter time with a higher accuracy and at a lower cost.

This objective is accomplished inventively by means of the process described at the outset owing to the fact that metal particles are added to a specified amount of the dry, milled soil sample and the dry matter is heated inductively in the presence of the reactant to the reaction temperature.

The inductive heating is accomplished preferably by means of an induction coil supplied with high frequency (HF) and surrounding the sample. Such a "high-frequency furnace", including the associated analytical equipment, is commercially available and is manufactured, for example, by Leybold-Heraeus GmbH in Hanau, Federal Republic of Germany, under the name of "CSA 302". This analytical equipment is, however, intended for the analysis of strictly metallic samples.

It was now, however, surprisingly shown that, by the addition of metal particles to soil samples, which are not inductively heatable per se, largely homogeneous, rapid and reproducible heating of the soil samples is possible and very accurate analytical results are obtained within a period of less than 1 minute.

The sole figure is a graph illustrating a comparison of $CaCO_3$ content values obtained from the inventive method and the prior wet chemistry method.

The inventive method can be differentiated with respect to the reactants as follows:

In a method for the determination of the total content of carbon compounds by combustion, the inventive procedure is such that the proportion of metal particles in the mixture is selected to be between 50 and 95 percent by weight and the reaction is carried out in a stream of oxygen and at a temperature, at which all of the carbon compounds are converted into carbon dioxide.

In this case, the oxygen constitutes not only the reactant, but also the carrier gas, by means of which the carbon dioxide, formed from a part of the oxygen by combustion, is conveyed to the analyzer. It follows from this that the oxygen is added in an excess relative to the stochiometrical relationships.

In a method for the determination of the carbonate content by reaction of the carbonates with an acid, the inventive procedure is such that, aside from the metal particles, a solid, inorganic acid, which does not react with the matter at room temperature, is added in excess to a specified amount of dry, milled soil sample, the matter is heated to the reaction temperature and the carbon dioxide formed is supplied by means of a current of flushing, inert gas to the analyzer.

As inorganic acid, essentially anhydrous, orthophosphoric acid is preferably used here. This acid is solid or crystalline at room temperature and has a low melting point of 42.3° C. In the molten state, it has a sufficiently low viscosity to enable the carbonates to be converted completely to carbon dioxide and the corresponding phosphates. This conversion takes place within 40 to 50 seconds, so that it is possible to read the test or calculated result within less than 60 seconds. The reaction moreover takes place at temperatures not exceeding 280° C., so that any humus present is not attacked in such a manner, that carbon dioxide, released from it, could distort the test result.

The reaction itself is advisably carried out in an appropriately resistant ceramic crucible, which itself is not coupled to the high frequency source and, in other respects, also does not affect the reaction disadvantageously.

The carbonates, which are converted by the inventive reaction with acid, are, for example, the carbonates of calcium ($CaCO_3$) and magnesium ($MgCO_3$) or mixed carbonates such as $CaMg(CO_3)_2$. These are the carbonates, which are predominantly found in arable soils.

The inventive acid reaction can be used wherever the carbonate content of soil samples is to be determined, namely for:

(a) soils used for agriculture and forestry,
(b) the starting material for the production of aluminum (bauxite),
(c) part of the total analysis to determine the humus content of soils.

The object of the invention has the advantage that the inventive combustion procedure, as well as the inventive acid reaction can be carried out in conjunction with one and the same analytical equipment. Such analytical equipment is sold by Leybold-Heraeus GmbH in Hanau, Federal Republic of Germany, under the name of "BINOS". It is a question here of an infrared gas analyzer with a microanemometer, which is described in detail in the BRD Patent 2,614,181. Only two high-frequency furnaces or one high-frequency furnace with the possibility of changing over from one gas to another (either oxygen or an inert gas, preferably nitrogen) are required for the inventive object.

As already stated above, the carbon dioxide content in the carrier gas is determined quantitatively in the analytical apparatus. This content must, of course, still be related to the amount of sample and to the particular carbonate present in the sample. This can be done by means of special factors, which are stored in a computer that forms a part of the analytical equipment.

Numerous metals come into consideration as metal particles, provided that they themselves do not produce interfering reaction products or lead to undesirable side reactions. Preferably, copper powder comes into consideration. However, particles of ferromagnetic metals may also be employed. The coupling of these particles to the high-frequency field decreases with increasing temperature, as is the case, for example, when the Curie temperature is exceeded. When such a metal is used, automatic temperature stabilization advantageously results with an upper temperature limit that can be fixed by the selection of the Curie point.

In the following, it is demonstrated by means of a comparison diagram that the analytical results agree very well with those, which were previously obtained by the cumbersome, wet-chemical method, which has already successfully found acceptance in practice.

To avoid inhomogeneities within the samples, it is particularly advantageous to mill a larger amount of the soil sample, for example in a ball mill, to analyze several aliquots of this individually and to determine the average value from the analytical results. The appropriate sample weight is between about 0.2 and 1.0 g, depending on the size of the analytical crucible. Advantageously, distinctly larger amounts of metal particles and acid (for the acid reaction) are added to the soil sample, so that the proportion of soil sample in the total mass, produced by mixing, lies between 5 and 20 weight percent.

To carry out the acid reaction, it is particularly advantageous if the proportion of metal particles is between 10 and 30 weight percent, the proportion of orthophosphoric is between 60 and 80 weight percent and the proportion of soil sample is at least 5 weight percent of the total mass.

To some extent, the orthophosphoric acid is hygroscopic, so that special precautionary methods must be employed while it is being weighed out. It is therefore advisable to keep on hand portions, weighed out in the absence of humidity, in hermetically sealed containers or to introduce the acid in capsule form. In so doing, care must be taken that any attendant materials, used to keep out the humidity, do not absorb or release carbon dioxide.

Oxygen is, of course, not suitable as a carrier gas for the acid reaction, since any oxidative process must be prevented during this reaction. Inert gases, preferably nitrogen, such as is commercially obtainable in cylinders, is therefore to be used as carrier gas.

EXAMPLE 1 (SAMPLE PREPARATION)

Air-dried soil (100 g) was milled for 10 minutes in a ball mill of the "Pulverisette" type (manufacturer: Fritsch, Federal Republic of Germany). The analytical material, obtained in this manner, consequently possessed a sufficient degree of fineness and homogeneity for the analytical procedure described below.

Example 2 (Combustion)

The analytical material (200 g), described above, was mixed with 1,000 g of pure iron powder and added to an analytical ceramic crucible with a capacity of 5 cc. The crucible was placed in the water-cooled high-frequency coil of an analytical furnace, which was accommodated in a gas-tight chamber. This chamber and the analytical apparatus ("BINOS") connected to it by means of a pipeline, were first of all flushed with pure oxygen without heating the sample. The oxygen was supplied via a lance, the outlet of which was located above the sample in the analytical crucible. After adequate flushing, the high-frequency coil was connected to the associated high-frequency generator, whereupon, after a heating time of 2–3 seconds, the combustion process commenced, accompanied by strongly luminous phenomena. The carbon dioxide released here, together with the oxygen supplied in excess (approximately 40 mL/sec) as flushing gas, was passed through the analytical equipment, the carbon dioxide portion was determined and, after appropriate conversion, was shown as the carbonate content of the sample.

Example 3 (Acid Reaction)

A new analytical crucible, with a sample weight of 200 mg of a sample similar to that of Example 1, was placed in the same analytical equipment used in Example 2, 400 mg of fine copper powder and 1,900 mg of orthophosphoric acid being added to this sample. Before the high-frequency generator was switched on, the whole of the apparatus was flushed carefully with nitrogen. In the crucible, there was a thermocouple to monitor the maximum temperature of the reaction mixture. The high-frequency generator was then switched on, which manifested itself in a rise in temperature. After 20 seconds, first a melting and then a foaming of the reaction mixture was observed. The amount of carrier gas (nitrogen) supplied over the lance, was 50 mL/sec. After 45 seconds, foaming had ceased and the indicator of the analytical instrument showed that the transport of carbon dioxide had stopped. The reading of the end result was available after 55 seconds.

Example 4 (Comparison Experiment)

As in Example 3, numerous samples of different soils were investigated in the form of sample mixtures with the same proportion of components (copper and acid) and at the same flow rate of flushing gas. Parallel to this, identical soil samples were investigated by the classical, wet-chemical procedure of "Scheibler". For comparison purposes, the analytical values were plotted in the graph below, in which the abscissa and the ordinate are the carbonate content in weight percent of the whole sample. The abscissa values originated from the conventional, wet-chemical procedure, while the ordinate values were obtained with the inventive procedure, carried out as in Example 3. The regression is $r=0.997$, the constant is $-0.0636$ and the first order is 1.018. In other words, the correlation coefficient of $r=0.997$ shows the good agreement of the values for which the "Scheibler" method was used with the values for which the inventive method was used. The constant of $-0.0636$, states that no systematic deviations occur between the two analytical methods over the whole of the concentration range. This shows clearly that the correlation of all analytical values is very good and adequate for practical purposes.

The terms and expressions which are employed are used as terms of description and not of limitation, and there is no intention in the use of such terms and expressions of excluding any equivalents of the features shown and described or portions thereof, it being recognized that various modifications are possible within the scope of the invention.

We claim:

1. A method for the determination of the content of solid carbon compounds in a dry soil sample comprising: inductively heating said dry soil sample with a metal particle reactant and an additional reactant selected from the group consisting of oxygen and an ACID to convert the solid carbon compounds into carbon dioxide and conveying the carbon dioxide gas into an analyzer which measures said carbon dioxide gas said carbon dioxide gas being representative of the content of solid carbon compounds in said sample.

2. The method of claim 1 wherein said metal particle reactant comprises between 50 and 95 weight percent of the total weight of said metal particle reactant, said additional reactant and said dry soil sample.

3. Method as defined in claim 1, wherein the metal particle reactant comprises copper.

4. The method of claim 1, wherein said conveying of said carbon dioxide to said analyzer is done by flushing with an inert gas.

5. The method of claim 1 further comprising adding an inorganic acid to said sample, wherein said inorganic acid is a solid that does not react with a component of said dry soil sample at room temperature but forms carbon dioxide by reaction with said solid carbon compounds at a reaction temperature brought about by said inductive heating said inorganic acid being added in excess to said dry soil sample.

6. Method of claim 5, wherein said inorganic acid is an essentially anhydrous orthophosphoric acid.

7. Method of claim 6, wherein the proportion of said metal particle reactant is between 10 and 30 weight percent, the proportion of said orthophosphoric acid is between 60 and 80 weight percent and the proportion of said dry soil sample at least 5 weight percent of the total sample.

8. A method for the determination of the content of solid carbon compounds in a soil sample comprising:
   drying and milling a soil sample;
   adding a metal particle reactant and an additional reactant selected from the group consisting of oxygen and an acid to the dried soil sample;
   inductively heating the dried soil sample with the metal particle reactant and the additional reactant to convert solid carbon compounds of the soil sample into carbon dioxide; and
   conveying the carbon dioxide gas into an analyzer to measure the carbon dioxide gas, said carbon dioxide gas being representative of the solid carbon compounds in the soil sample.

* * * * *